United States Patent [19]
Kohl

[11] Patent Number: 5,168,870
[45] Date of Patent: Dec. 8, 1992

[54] DEFIBRILLATOR

[75] Inventor: Martin Kohl, Braeuningshof, Fed. Rep. of Germany

[73] Assignee: Siemens Aktiengesellschaft, Munich

[21] Appl. No.: 788,024

[22] Filed: Nov. 5, 1991

[30] Foreign Application Priority Data

Nov. 29, 1990 [DE] Fed. Rep. of Germany ....... 4038105

[51] Int. Cl.$^5$ .............................................. A61N 1/39
[52] U.S. Cl. ............................................... 128/419 D
[58] Field of Search .................................. 128/419 D

[56] References Cited

U.S. PATENT DOCUMENTS

| | | | |
|---|---|---|---|
| 4,077,413 | 3/1978 | Partridge | 128/419 D |
| 4,168,711 | 9/1979 | Cannon, III et al. | 128/419 D |
| 4,771,781 | 9/1988 | Lerman | 128/419 D |

FOREIGN PATENT DOCUMENTS

| | | |
|---|---|---|
| 0060404 | 9/1982 | European Pat. Off. |
| 0315368 | 5/1989 | European Pat. Off. |
| 2085593 | 4/1982 | United Kingdom |

OTHER PUBLICATIONS

"A Reliable Microprocessor-Based Defibrillator Analyzer" Sharma et al. IEEE Trans. on Instr. and Meas. vol. IM-31, No. 1, Mar., 1982, pp. 28-31.

"Thoracic Impedance of Human Subjects," Machin, Med. and Biol. Eng. and Comp. vol. 16, No. 2, Mar. 1978, pp. 169-178.

*Primary Examiner*—William E. Kamm
*Assistant Examiner*—Scott M. Getzow
*Attorney, Agent, or Firm*—Hill, Van Santen, Steadman & Simpson

[57] ABSTRACT

A defibrillator has a storage capacitor and a coil which are adapted for connection to biological tissue to form an RLC circuit through which a signal is discharged to the biological tissue. A measuring stage is coupled to the RLC circuit via a transformer for measuring selected characteristics of the signal. The coil is formed by a primary winding of the transformer, the primary winding thus providing the inductance for the RLC circuit. By incorporating the function of the coil into the transformer, the space necessary for a separate component is avoided and the overall structure can be made smaller.

8 Claims, 2 Drawing Sheets

DEFIBRILLATOR

BACKGROUND OF THE INVENTION

1. Field of the Invention

The present invention is directed to a defibrillator of the type having a storage capacitor and a coil that are connectable via biological tissue to form an RLC discharge circuit, to which a measuring stage is coupled via a transformer.

2. Description of the Prior Art

A defibrillator serves the purpose of terminating ventricular fibrillation with an electrical pulse (electric shock). To that end, electrical energy that is stored in a storage capacitor (discharge capacitor) is supplied to biological tissue, for example, heart muscle tissue, via an induction coil in a discharge circuit. The desired curve (shape) of the electrical pulse is essentially defined by the coil. In order to be able to identify the output electrical energy and/or the resistance of the patient tissue, a transformer for coupling-out a measured signal is additionally provided in a branch of the discharge circuit that is connectable to the patient via electrodes, this transformer having its secondary side connected to a measuring shape. The coupling-out transformer is fashioned as a current transformer. The measuring shape measures the peak value occurring at the secondary side of the transformer. The patient resistance and/or the output energy to the patient are identified from the measured peak value with, for example, a microprocessor, and taking the energy stored in the storage capacitor into consideration. In such a defibrillator, the space required for the necessary component parts in the discharge circuit is problematical, particularly when the defibrillator must be implantable into the patient. The weight of the defibrillator also increases with the size and number of component parts.

SUMMARY OF THE INVENTION

In a defibrillator of the type described above, it is an object of the present invention to reduce the space required for the necessary component parts, particularly in the discharge circuit.

The above object is achieved in accordance with the principles of the present invention in a defibrillator having a storage capacitor and a coil adapted for connection to biological tissue to form an RLC circuit through which a signal is discharged to the biological tissue. A measuring stage is provided for measuring selected characteristics of the signal. The measuring stage is coupled to the RLC circuit by a transformer. The coil is formed by a primary winding of the transformer, so that the primary winding provides the inductance for the RLC circuit.

A significant advantage of the invention is that the space required for the necessary component parts in the discharge circuit is significantly diminished. This is particularly achieved by a physical and functional combination of two discrete component parts, i.e., a separate induction coil and primary winding of the coupling-out transformer, to form a unitary component. To that end, the necessary inductance in the discharge circuit for generating the desired pulse shape of the electrical pulse that can be supplied to the patient is formed only by the primary winding of the coupling-out transformer in the discharge circuit. A further space saving can be achieved by fashioning the transformer as an air-core transformer. Compared to transformers having a ferrite core or the like, this also achieves a considerable saving in weight.

In an advantageous embodiment of the invention, the transformer has an inductance at the secondary side that is selected small in comparison to the inductance of the coil at the primary side. As a result, the weight and the size, and thus the space requirement, of the transformer can again be reduced. The primary winding and secondary winding of the transformer can be arranged concentrically relative to one another. As a result, a compact, space-saving format is achieved, particularly when the primary winding is fashioned as an inner winding and the secondary winding is fashioned as an outer winding of the transformer.

DESCRIPTION OF THE PREFERRED EMBODIMENTS

Figure 1:
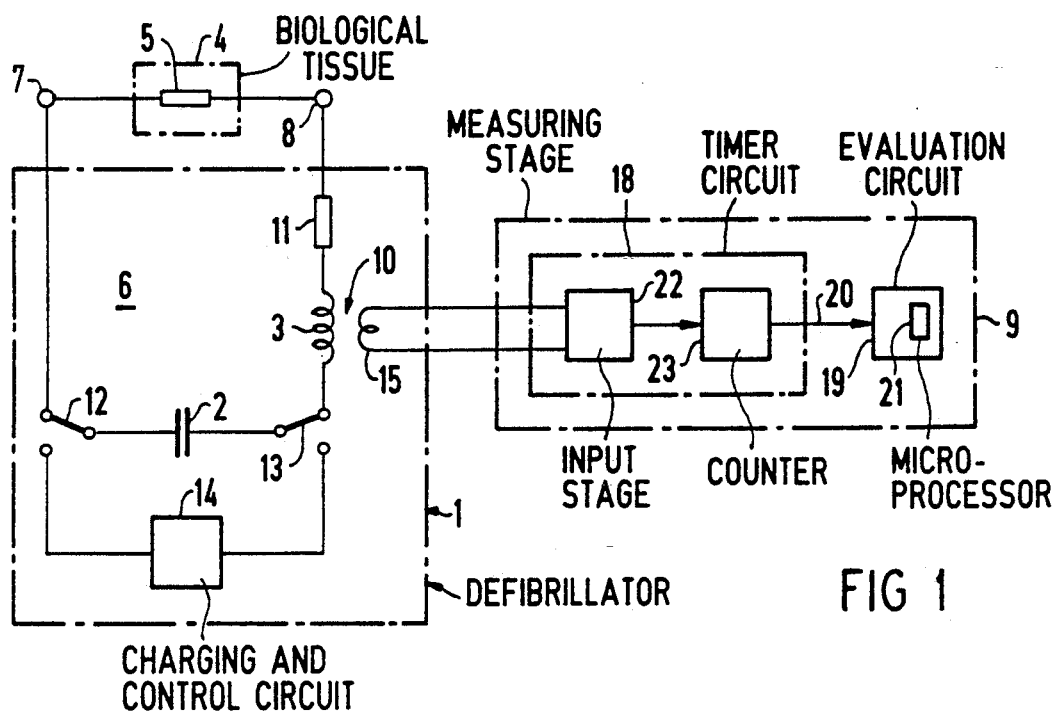
FIG. 1 is a schematic block diagram of a defibrillator constructed in accordance with the principles of the present invention.

FIG. 1 shows a defibrillator 1 having a storage capacitor 2 and a coil 3. The storage capacitor 2 and the coil 3 are connectable to form an RLC discharge circuit 6 via biological tissue 4 of a patient that has a patient resistance 5. Particularly given defibrillators that are not implanted in the patient, the connection to the biological tissue 4 of the patient can occur via electrodes 7 and 8 that can be placed against the skin of the patient. A measuring stage 9 is coupled via a transformer 10 to the RLC discharge circuit 6. The coil 3 is thereby fashioned as the primary winding of the transformer 10. This primary winding 3 has the necessary inductance of the RLC discharge circuit 6 with which the desired shape of the electrical pulse supplied to the patient is essentially defined.

Further, a resistor 11 is also shown in the RLC discharge circuit 6, this resistor 11 symbolizing the internal resistance of the coil 3, i.e. the internal resistance of the primary winding of the transformer 10. This resistor 11 and the patient resistance 5 define the time at which a current maximum of the electrical pulse output to the biological tissue 4 is reached.

The storage capacitor 2 is connectable to a charging and control circuit 14 for charging via switches 12 and 13, which can be electronically fashioned and controlled. The charging and control circuit 14 serves the purpose of charging the storage capacitor 2 and controlling the switches 12 and 13. The output of an electrical pulse from the RLC discharge circuit 6 to the biological tissue 4 is thereby also controllable.

The transformer 10 in the exemplary embodiment of FIG. 1 is fashioned as a voltage transformer. The load resistor at the secondary side of the transformer, required for a current transformers, is thereby eliminated.

This leads to a further saving in space and weight. A further improvement is achieved when the secondary winding 15 of the transformer 10 has an inductance that is selected small in comparison to the inductance of the primary winding 3.

The dimensions of the transformer 10 can also be reduced in that the transformer 10 is essentially fashioned (i.e., has a transfer function) for no-load operation and is high-impedance coupled to the measuring stage 9. A further saving in weight and space is achieved by making the transformer an air-core transformer. Due to the high-impedance coupling of the transformer to the measuring means 9, the inductance of the secondary winding 15 of the transformer 10 can already be realized with few turns, for example two turns. The inductance of the primary winding 3, for example, can be 32 mH, the capacitance of the storage capacitor 2 can be approximately 32 $\mu$F and the value of the resistor 11 can be approximately 25 ohms.

Figure 2:
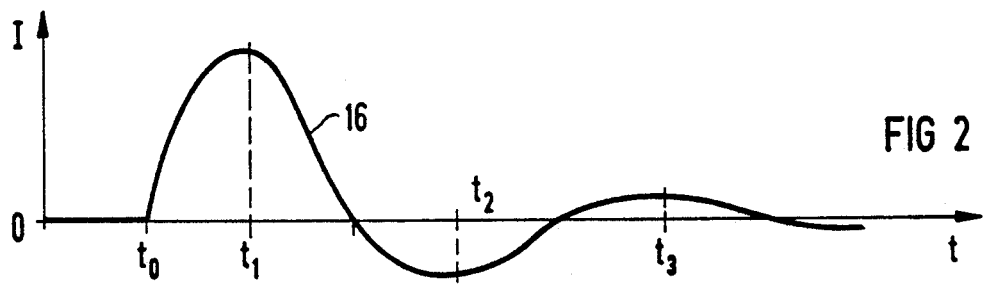
FIG. 2 is an aperiodically attenuated oscillation signal that can be supplied to biological tissue as an electrical pulse by the defibrillator of FIG. 1.
Figure 3:
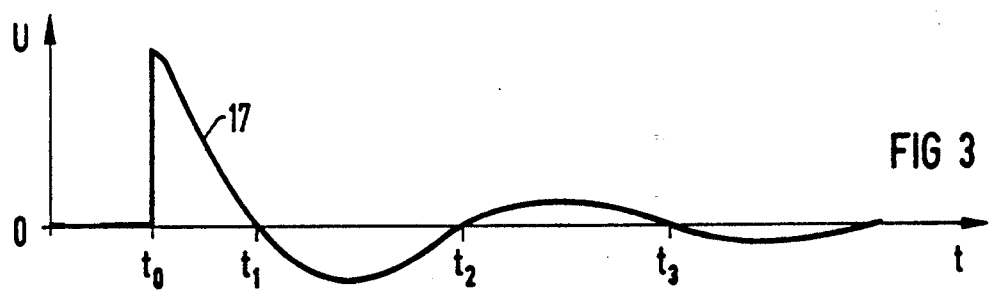
FIG. 3 is a signal at the secondary side of the transformer of the defibrillator of FIG. 1 that is differentiated from the electrical pulse of FIG. 2.

In the illustrated exemplary embodiment, the transformer provided in the defibrillator of the invention effects a differentiation of the electrical pulse 16 that is shown by way of example in FIG. 2, and can be supplied to the biological tissue 4. A differentiated signal 17 according to the illustration in FIG. 3 is consequently formed at the secondary winding of the transformer 10 in FIG. 1. Consequently, every turning point in the curve 16 at times $t_1$, $t_2$ or $t_3$ in FIG. 2 respectively corresponds to a zero-axis crossing of the curve 17 at the times $t_1$, $t_2$ or $t_3$ in FIG. 3. This effect of the present invention is exploited in that the measuring stage 9 includes a timer circuit 18, with which the chronological spacing between two electrical values, transmittable from the transformer in the electrical pulse 16 to the biological tissue 4, can be measured. Such a timer circuit can be realized with commercially available small components using little space. The measurement of the chronological spacing between the values $t_0$ and $t_1$ of the curve 17 (differentiated signal) of FIG. 3 can thereby be realized with particular precision and with little outlay. The resistance 5 of the biological tissue 4 can then be identified from the chronological spacing between two characteristic values of the electrical pulse 16. Consequently, a high measuring precision can also be achieved given low space requirement.

The measuring stage 9 coupled to the RLC discharge circuit 6 of FIG. 1 via the transformer 10 includes an evaluation circuit 19. The value of the resistance 5 of the biological tissue 4 is identified, for example with the assistance of a microprocessor 21, in the evaluation circuit 19 from a timing signal received via the line 20 from the timer circuit 18.

The timer circuit 18 can contain a plurality of stages. An input stage 22 serves the purpose of recognizing characteristic (measurable) values of the electrical pulse 16 that can be supplied to the biological tissue 4, or in the differentiated signal 17. Dependent on such characteristic values that have been recognized, the input stage 22 can then control a counting circuit 23 that, for example, counts clock pulses. Thus, the counter circuit 23 can be started, for example, by the voltage peak of the differentiated signal 17 arising at time $t_0$ and can be stopped given the presence of a second characteristic value, for example, the zero-axis crossing at time $t_1$. The number of counted pulses represents a measure (timing signal) for the chronological duration between the two characteristic values.

In order to calibrate the measuring stage 9 of the defibrillator 1, the manufacturer can first arrange high-precision resistors between the electrodes 7 and 8 and the times between two characteristic values measured upon the output of an electrical pulse 17 in the evaluation circuit 19 can be stored in the microprocessor 21, for example as a value table in relation to the value of the precision resistor. Intermediate values can be calculated by interpolation and stored. However, it also possible to calculate the chronological duration until a characteristic value of the pulse 16 is reached in the microprocessor 21 dependent on the changing value of the resistance 5 and dependent on the electrical values of the primary winding 3, of the resistor 11 and of the capacitor 2. The mathematical bases regarding the behavior of a RLC discharge circuit are known, for example, from the periodical "International Medical Device and Diagnostic Industry", May/June 1990, page 48.

Figure 4:
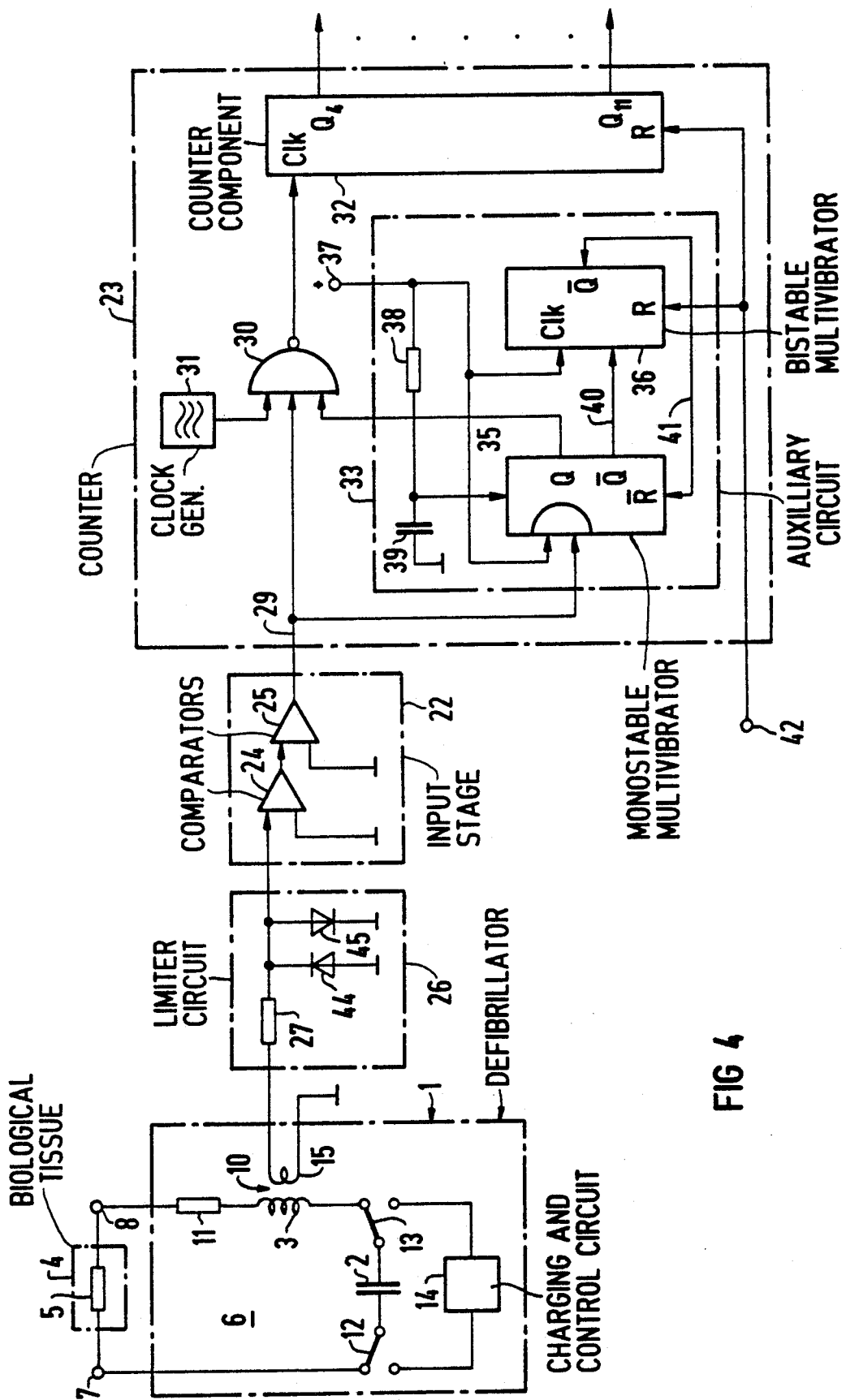
FIG. 4 is a partial circuit diagram of the defibrillator of FIG. 1 showing a more detailed illustration of a timer circuit.

FIG. 4 shows the counter circuit 23 and the first stage 22 of the timer circuit 18 described with respect to FIG. 1 as a specific exemplary embodiment. The stage 22 contains two comparators 24 and 25 that are connected via a limiter circuit 26 to the RLC discharge circuit 6 in the defibrillator 1 described with respect to FIG. 1. The limiter circuit 26 contains a limiting resistor 27 and two diodes 44 and 45 connected with opposite polarity. The voltage peak of the differentiated signal 17 following the time $t_0$ in FIG. 3 is limited with the limiter circuit 26 (but this is not absolutely necessary). The input of the following comparator circuit 24 is thereby protected against over-voltages. The output of the comparator 24 is connected to an input of the comparator 25. Every zero-axis crossing of the differentiated signal according to curve 17 in FIG. 3 is consequently identified with particular precision.

Figure 5:
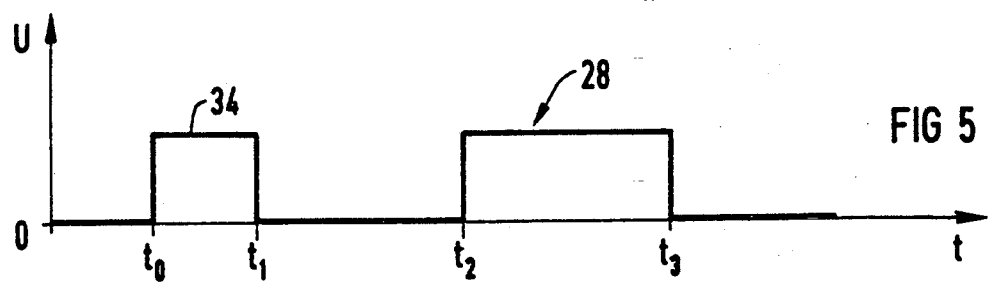
FIG. 5 is a square-wave signal that is generated within the timer circuit of FIG. 4.

As a result of the specific fashioning of the stage 22 of FIG. 4, a square-wave signal 28 that is shown in FIG. 5 arises at the output thereof. A gate circuit in the counter 23 is driven (FIG. 4) with this square-wave signal 28 via a line 29. The gate circuit 30 receives clock pulses from a clock generator 31 via another input. The clock pulses are counted in a counter module 32 during the chronological duration during which the gate circuit 30 had been opened by, for example, the square-wave signal 28 on the line 29 (particularly by the individual pulse 34). For example, an 11-bit counter IC having the type designation 4020 is suitable as the counter 23, this integrated circuit 4020 having parallel outputs $Q_4$ through $Q_{11}$. The electrical output signal from the counter 32 can then be supplied (via an appropriately multi-poled line 20) to the evaluation circuit 19 for the calculation of a parameter, as already mentioned with respect to the description of FIG. 1.

When the electrical pulse that can be supplied to the biological tissue 4 has the shape of an attenuated oscillation according to the curve 16 in FIG. 2, it is expedient to provide an auxiliary circuit 33 according to FIG. 4. The gate circuit 30 is additionally controlled such with this auxiliary circuit 33 so that counting pulses from the clock generator 31 of FIG. 4 can proceed to the counter component 32 only during the chronological duration of a first pulse 34 ($t_0$ through $t_1$) of the square-wave signal 28 of FIG. 5. To this end, the auxiliary circuit 33 comprises two trigger circuits. One trigger circuit is fashioned as a monostable multivibrator 35 and another trigger circuit is fashioned as a bistable multivibrator 36. The monostable multivibrator 35 receives a positive operating voltage via the terminal 37. The positive operating voltage also feeds an RC element formed of a resistor 38 and a capacitor 39. The monostable multivibrator 35 is started by the first edge at the time $t_0$ of the pulse 34 of the square-wave signal 28 that arises on the line 29 when a pulse 16 is supplied to the biological tissue 4. An output signal, with which the gate circuit 30 is opened during the hold time of the multivibrator 35 set by the R elements 38 and 39, is thereby generated at an output Q of the multivibrator 35. An inverting output Q of the multivibrator 35 is connected via a line 40 to a control input CLK of the bistable multivibrator 36. The bistable multivibrator 36 then inhibits the monostable multivibrator 35 via a line 41, so that the latter can no longer be triggered by pulses which may possibly follow the square-wave signal 28. Before supplying another electrical pulse 16 to the biological tissue 4, the auxiliary circuit 33 and the counter 32 can be reset into their initial conditions by a reset signal, for example from the charging and control circuit 14, that can be supplied via the terminal 42. For example, a component having the type designation 4538 can be employed as the monostable multivibrator 35 and a component having the type designation 4013 can be employed as the bistable multivibrator.

Although modifications and changes may be suggested by those skilled in the art, it is the intention of the inventor to embody within the patent warranted hereon all changes and modifications as reasonably and properly come within the scope of his contribution to the art.

I claim:

1. A defibrillator comprising: a storage capacitor and a coil adapted for connection to biological tissue to form an RLC circuit through which a signal is discharged to said biological tissue; measuring means, coupled to said RLC circuit via an air-core transformer, for measuring selected characteristics of said signal; and said coil being formed by a primary winding of said air-core transformer, said primary winding providing the inductance for said RLC circuit.

2. A defibrillator as claimed in claim 1 wherein said transformer has an inductance at a secondary side which is small compared to the inductance of said primary winding.

3. A defibrillator as claimed in claim 1 wherein said transformer has a transfer function for no-load operation and is high-impedance coupled to said measuring means.

4. A defibrillator as claimed in claim 1 wherein said transformer is a voltage transformer.

5. A defibrillator as claimed in claim 1 wherein said transformer has a secondary winding and where said primary winding and said secondary are disposed concentrically relative to each other.

6. A defibrillator as claimed in claim 5 wherein said primary winding is an inner winding and said secondary winding is an outer winding of said transformer.

7. A defibrillator as claimed in claim 1 wherein said measuring means is a timer circuit means for measuring the chronological duration between two selected electrical values of said signal.

8. A defibrillator as claimed in claim 7 wherein said measuring means includes means for measuring the value of the resistance of said biological tissue from said chronological duration between said electrical values of said signal.

* * * * *